(12) United States Patent
Bonutti

(10) Patent No.: US 8,128,669 B2
(45) Date of Patent: Mar. 6, 2012

(54) METHOD OF SECURING TISSUE

(75) Inventor: Peter M. Bonutti, Effingham, IL (US)

(73) Assignee: P Tech, LLC., Effingham, IL (US)

( * ) Notice: Subject to any disclaimer, the term of this patent is extended or adjusted under 35 U.S.C. 154(b) by 300 days.

(21) Appl. No.: 11/067,911

(22) Filed: Feb. 28, 2005

(65) Prior Publication Data

US 2005/0149029 A1 Jul. 7, 2005

Related U.S. Application Data

(63) Continuation of application No. 10/007,360, filed on Oct. 29, 2001, now Pat. No. 6,860,885, which is a continuation of application No. 09/370,865, filed on Aug. 9, 1999, now Pat. No. 6,447,516.

(51) Int. Cl.
*A61B 17/04* (2006.01)
(52) U.S. Cl. ...................................................... 606/300
(58) Field of Classification Search .............. 606/72–74, 606/300–321, 86, 96–100, 104, 105, 62–68, 606/86 R
See application file for complete search history.

(56) References Cited

U.S. PATENT DOCUMENTS

| | | | |
|---|---|---|---|
| 2,187,852 A | 1/1940 | Friddle | |
| 2,235,419 A | 3/1941 | Callahan | |
| 2,270,188 A | 1/1942 | Longfellow | |
| 2,557,669 A | 6/1951 | Lloyd | |
| 2,621,653 A | 12/1952 | Briggs | |
| 2,725,053 A | 11/1955 | Bambara et al. | |
| 3,809,075 A | 5/1974 | Matles | |
| 3,842,824 A * | 10/1974 | Neufeld | 606/73 |
| 2,121,193 A | 6/1983 | Hanicke | |
| 4,772,286 A * | 9/1988 | Goble et al. | 623/13.14 |
| 4,776,328 A * | 10/1988 | Frey et al. | 606/326 |
| 4,776,851 A | 10/1988 | Bruchman et al. | |
| 4,790,303 A | 12/1988 | Steffee | |
| 4,834,752 A | 5/1989 | Van Kampen | |
| 4,869,242 A | 9/1989 | Galluzzo | |
| 5,013,316 A | 5/1991 | Goble et al. | |

(Continued)

OTHER PUBLICATIONS

David E. Taylor et al., Technical Note, entitled: Femoral Bone Plug Recession in Endoscopic Anterior Cruciate Ligament Reconstruction, Arthroscopy: The Journal of Arthroscopic and Related Surgery, vol. 12, No. 4, Aug. 1996: pp. 513-515.

(Continued)

*Primary Examiner* — Eduardo C Robert
*Assistant Examiner* — Tara Carter
(74) *Attorney, Agent, or Firm* — Fleit Gibbons Gutman Bongini & Bianco, PL; Paul D. Bianco; Martin Fleit

(57) ABSTRACT

A retainer member formed of bone secures tissue relative to a bone. The retainer member forms an opening in a compact outer layer of the bone. The retainer member is enclosed in a tubular member or sleeve to prevent breaking of the retainer member during formation of the opening in the bone. The extent of movement of the retainer member into the hone in the patient's body is determined as the retainer member is moved into the bone. A suture may be connected with the retainer member and used to connect tissue with the bone. The retainer member may be positioned across a fracture in a bone to hold portions of the hone relative to each other. The retainer member may be used at a joint between end portions of bones to immobilize the joint and be released by breaking the retainer member.

35 Claims, 6 Drawing Sheets

U.S. PATENT DOCUMENTS

| | | | |
|---|---|---|---|
| 5,059,206 A | 10/1991 | Winters | |
| 5,078,745 A | 1/1992 | Rhenter | |
| 5,098,434 A | 3/1992 | Serbousek | |
| 5,147,362 A * | 9/1992 | Goble | 606/72 |
| 5,203,784 A * | 4/1993 | Ross et al. | 606/104 |
| 5,330,476 A | 7/1994 | Hiot et al. | |
| 5,352,229 A | 10/1994 | Goble et al. | |
| 5,527,343 A | 6/1996 | Bonutti | |
| 5,529,075 A | 6/1996 | Clark | |
| 5,534,012 A | 7/1996 | Bonutti | |
| 5,569,252 A | 10/1996 | Justin et al. | |
| 5,601,558 A | 2/1997 | Torrie et al. | |
| 5,609,595 A | 3/1997 | Pennig | |
| 5,626,612 A | 5/1997 | Bartlett | |
| 5,693,055 A | 12/1997 | Zahiri et al. | |
| 5,713,903 A | 2/1998 | Sander et al. | |
| 5,741,282 A | 4/1998 | Anspach et al. | |
| 5,752,952 A | 5/1998 | Adamson | |
| 5,755,809 A | 5/1998 | Cohen et al. | |
| 5,823,994 A | 10/1998 | Sharkey et al. | |
| 5,868,749 A * | 2/1999 | Reed | 606/76 |
| 5,918,604 A * | 7/1999 | Whelan | 128/898 |
| 5,919,193 A | 7/1999 | Slavitt | |
| 5,921,986 A * | 7/1999 | Bonutti | 606/60 |
| 5,931,838 A * | 8/1999 | Vito | 606/61 |
| 5,931,869 A * | 8/1999 | Boucher et al. | 128/898 |
| 5,941,901 A | 8/1999 | Egan | |
| 5,948,000 A * | 9/1999 | Larsen et al. | 606/232 |
| 5,961,521 A | 10/1999 | Roger | |
| 5,968,046 A * | 10/1999 | Castleman | 606/73 |
| 5,968,047 A * | 10/1999 | Reed | 606/76 |
| 6,155,756 A | 12/2000 | Mericle et al. | |
| 6,187,008 B1 * | 2/2001 | Hamman | 606/318 |
| 6,547,792 B1 * | 4/2003 | Tsuji et al. | 606/72 |
| 2002/0016633 A1 | 2/2002 | Lin et al. | |
| 2002/0029084 A1 | 3/2002 | Paul et al. | |
| 2002/0062153 A1 | 5/2002 | Paul et al. | |

OTHER PUBLICATIONS

R. John Naranja, Jr. M.D. et al., A Review Paper entitled: The Search for the Holy Grail: a Century of Anterior Cruciate Ligament Reconstruction, The American Journal Of Orthopedics, Nov. 1997, pp. 743-752.

Walter R. Shelton, M.D. et al., Technical Note, entitled: Meniscus Replacement with Bone Anchors: A Surgical Technique, Arthroscopy: The Journal of Arthroscopic and Related Surgery, vol. 10, No. 3, 1994, pp. 324-327.

* cited by examiner

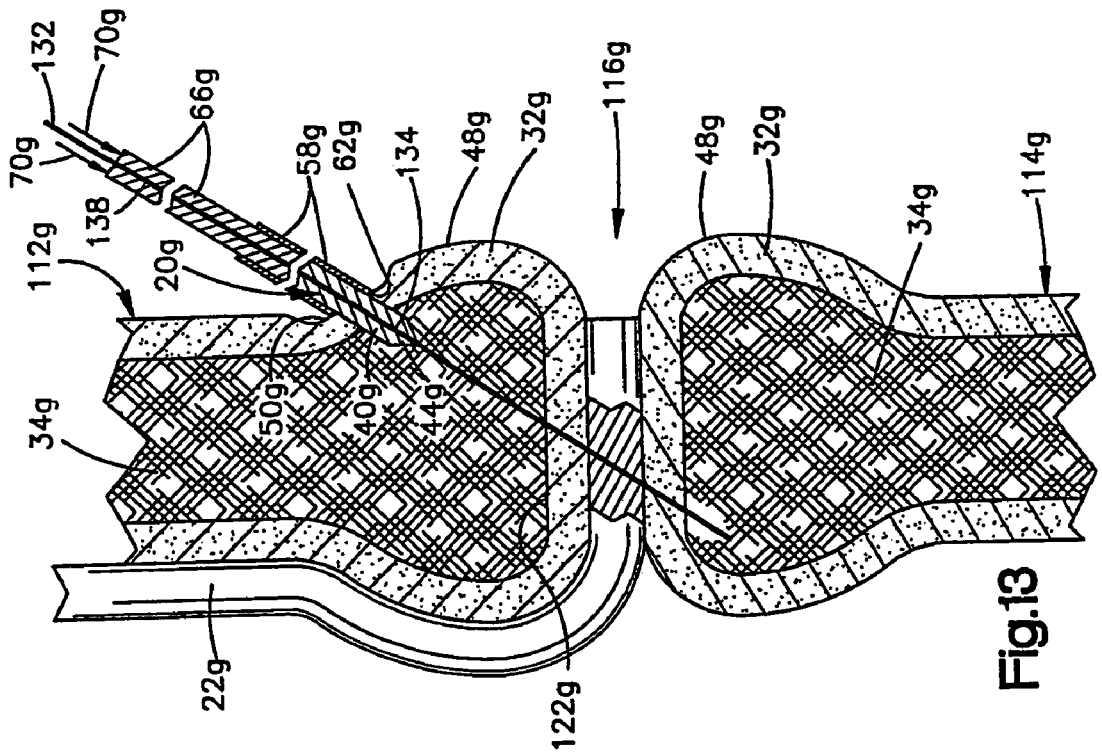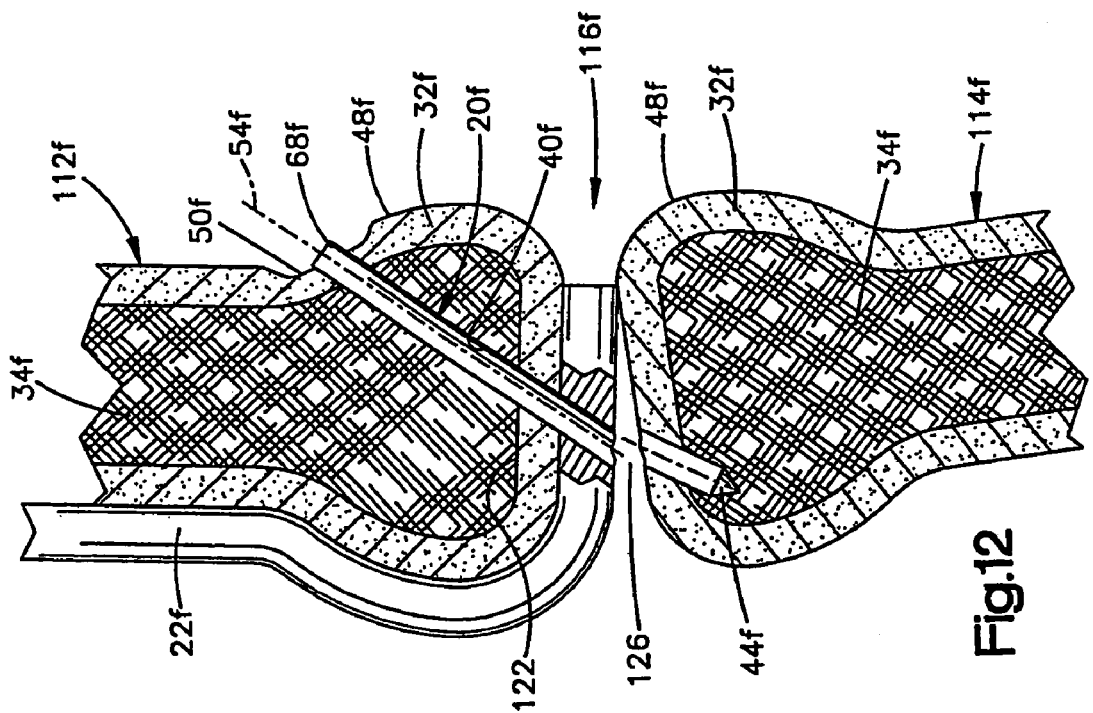

METHOD OF SECURING TISSUE

CROSS REFERENCE TO RELATED APPLICATIONS

This application is a continuation of U.S. patent application Ser. No. 10/007,360 filed Oct. 29, 2001 (now U.S. Pat. No. 6,860,885), which in turn is a continuation of U.S. patent application Ser. No. 09/370,865 filed Aug. 9, 1999 (now U.S. Pat. No. 6,447,516). The benefit of the earlier filing dates of each of the above-identified applications is hereby claimed. Furthermore, the content of each of the above-identified applications is incorporated herein by reference.

BACKGROUND OF THE INVENTION

The present invention relates to a new and improved method of securing tissue against movement relative to a portion of a bone in a patient's body.

Various tissue fixation systems have previously been utilized to hold portions of body tissue against movement relative to each other. When tissue is secured against movement relative to a portion of a bone, it is necessary to interconnect the bone and the tissue. In this situation, it has been a common practice to drill a hole which extends into or through the bone. A retaining member such as a pin, screw or suture anchor is positioned in the hole after it has been drilled in the bone. The concept of utilizing a retainer member formed of bone to anchor a suture is disclosed in U.S. Pat. No. 5,626,612.

SUMMARY OF THE INVENTION

The present invention relates to a new and improved method of securing tissue against movement relative to a portion of a bone in a patient's body. The method includes positioning a retainer member formed of bone in the portion of the bone in the patient's body and connecting the retainer member with the tissue to be secured. The step of positioning the retainer member formed of bone in the patient's body may include utilizing the retainer member to form an opening in a compact outer layer of the portion of the bone in the patient's body.

When the retainer member formed of bone is used to form an opening in the portion of the bone in the patient's body, the retainer member may advantageously be at least partially enclosed in a tubular member. Force may be applied against a trailing end portion of the retainer member formed of bone to force a leading end portion of retainer member into the portion of the bone in the patient's body. Movement of the retainer member into the portion of the bone in the patient's body may advantageously be interrupted when the leading end portion of the retainer member has moved to a predetermined depth in the bone in the patient's body.

The retainer member formed of bone may extend through and/or tension body tissue which is to be connected with the bone in the patient's body by the retainer member. The retainer member formed of bone may have a head end portion which engages body tissue. Alternatively, the retainer member formed of bone may be utilized to anchor a suture which is connected with body tissue. The retainer member formed of bone may be positioned in a bone in the patient's body so as to extend across a fracture and hold the portions of the bone on opposite sides of the fracture against movement relative to each other.

A retainer member, which may or may not be formed of bone, is utilized to immobilize a joint by having the retainer member extend between bones at the joint. If it is subsequently desired to release the joint for movement, the retainer member may be broken.

BRIEF DESCRIPTION OF THE DRAWINGS

The foregoing and other features of the invention will become more apparent upon a consideration of the following description taken in connection with the accompanying drawings wherein:

FIG. 12 is a schematic fragmentary sectional view illustrating the manner in which the retainer member of FIG. 11 is broken to release the joint for movement; and FIG. 13 is a schematic fragmentary sectional view, similar to FIG. 12, illustrating the manner in which a retainer member is moved into bones at a joint to immobilize the joint and hold tissue against movement relative to the joint.

DESCRIPTION OF SPECIFIC PREFERRED EMBODIMENTS OF THE INVENTION

Figure 1:
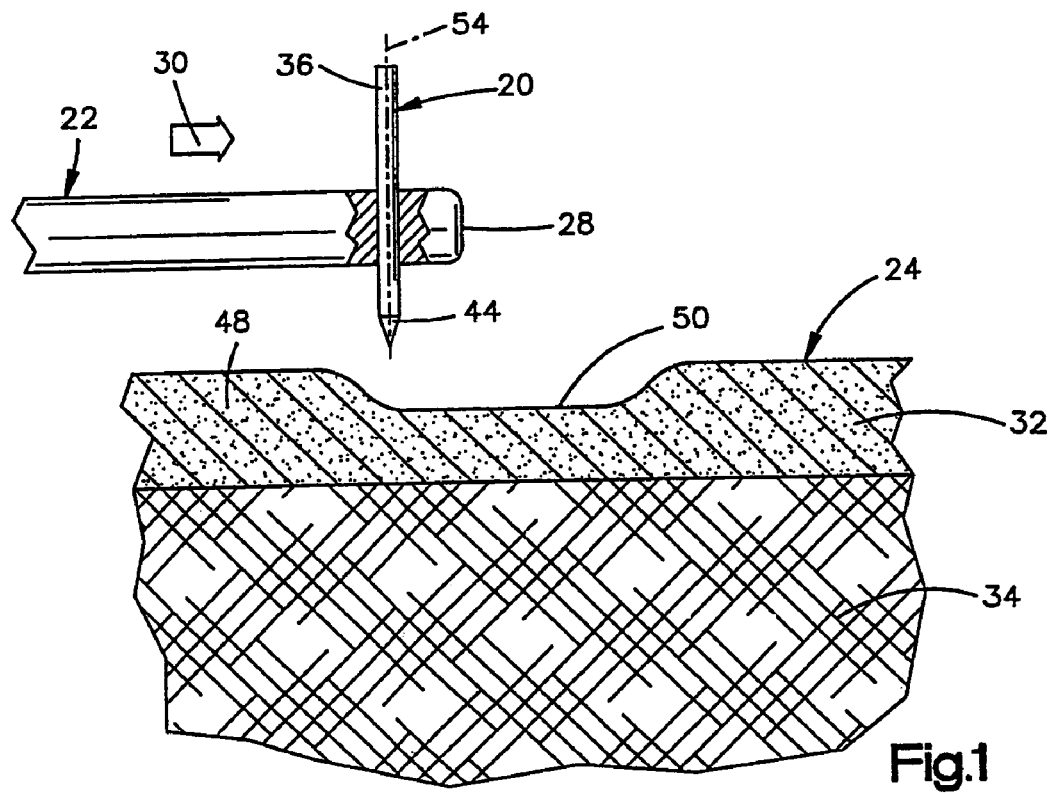
FIG. 1 is a fragmentary schematic sectional view illustrating engagement of a retainer member formed of bone with tissue which is to be tensioned and connected with a bone in a patient's body.
Figure 2:
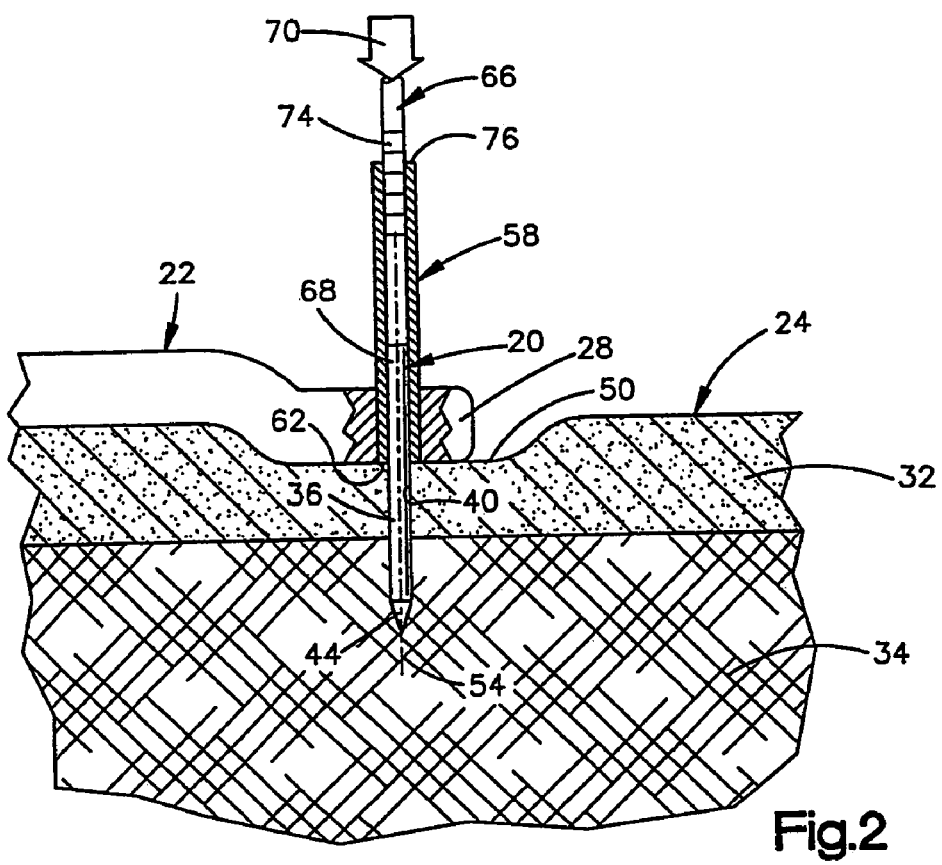
FIG. 2 is a schematic illustration, similar to FIG. 1, illustrating the manner in which the retainer member forms an opening in the bone in the patient's body.
Figure 3:
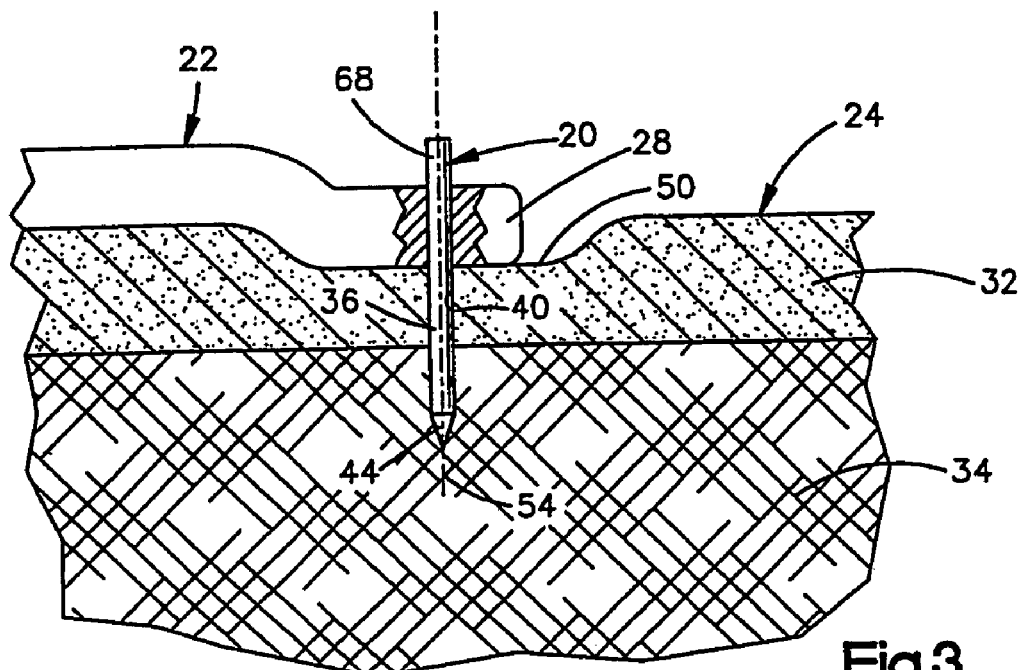
FIG. 3 is a schematic illustration, similar to FIGS. 1 and 2, illustrating the manner in which the tissue is connected with the bone by the retainer member.

Embodiment of FIGS. 1-3

In the embodiment of the invention illustrated in FIGS. 1-3, a retainer member 20 formed of bone is utilized to hold body tissue 22 against movement relative to a portion of a bone 24 in a human patient's body. The retainer member 20 may formed of bone which is allograft, autograft, or heterograft. However, it is contemplated that it may be preferred to form the retainer member 20 of freeze dried hard cortical bone.

The tissue 22 is connective tissue, such as a ligament or tendon. However, the tissue 22 could be other types of tissue if desired.

When the tissue 22 is to be connected with the bone 24, the retainer member 20 is inserted through an end portion 28 of the tissue 22. The retainer member 20 is then pulled toward the right (as viewed in FIG. 1), in the manner indicated by an arrow 30 in FIG. 1, to tension the tissue 22. The end portion 28 of the tissue 22 is moved rightward from an initial position (FIG. 1) to a connecting position (FIG. 2) as the tissue is tensioned.

The retainer member 20 is then positioned in the bone 24 in the patient's body in the manner illustrated in FIGS. 2 and 3. The retainer member 20 extends through a compact outer or cortical layer 32 of the bone into cancellous bone 34. A cylindrical outer side surface 36 (FIG. 3) on the installed retainer member 20 engages the end portion 28 of the tissue 22, the compact outer layer 32 of the bone 24, and the cancellous bone 34 to maintain tension in the tissue 22 and hold the tissue against movement relative to the bone 24. Although it is preferred to form the retainer member 20 with a cylindrical outer side surface 36 is contemplated that the retainer member 20 could have a different configuration if desired.

In accordance one of the features of the present invention, the retainer member 30 is utilized to form an opening 40 (FIGS. 2 and 3) at a location in the bone 24 where there is no naturally occurring opening (FIG. 1). Although it is preferred to initiate formation of the opening 40 with the retainer member 20 at a location in the bone 24 which is free of openings (FIG. 1), it is contemplated that a small opening could be predrilled through the compact outer layer 32 and into the cancellous bone 34 if desired. This small pilot opening would function to facilitate locating a leading end portion 44 of the retainer member 20 relative to the bone 24.

If a pilot opening is formed in the bone 24, the retainer member 20 would enlarge the pilot opening. As the pilot opening is enlarged by the retainer member 20, the opening 40 in the bone 24 would be formed to a configuration corresponding to the configuration of the outer side surface 36 of the retainer member. For example, if the retainer member 20 has a rectangular outer side surface 36 the opening 40 would be formed to have a rectangular cross-sectional configuration as the retainer member is moved into the pilot opening. Alternatively, if the retainer member 20 has a cylindrical outer side surface 36, the retainer member would form the opening 40 with a cylindrical side surface.

The illustrated retainer member 30 is a solid cylindrical body of hard cortical bone. However, it is contemplated that an axially extending passage could be formed through the retainer member 20. This axially extending passage would accept a long, thin guide member (not shown), such as a K-wire. The guide member, that is, the K-wire, would be utilized to initiate formation of a small opening extending through the compact outer or cortical layer 32 into the cancellous bone 34.

The retainer member 20 would then be moved along the guide member until the leading end portion 44 of the retainer member 20 engages the hard, compact outer layer 32 of the bone 24. The retainer member 20 would then be utilized to form an opening 40 in the compact outer layer 32 of the bone 24 with a cross-sectional configuration corresponding to the cross-sectional configuration of the retainer member. During formation of the opening 40 with the retainer member 20, the retainer member would be moved axially along the guide rod or wire. Once the retainer member 20 has been moved to a desired position relative to the bone 24, the guide wire or rod would be removed from the bone and from the retainer member.

In the embodiment of the invention illustrated in FIGS. 1-3, it is preferred to initiate formation of the opening 40 in the bone 24 with the retainer member 20. Prior to initiation of formation of the opening 40 with the retainer member 20, a hard outer surface 48 is removed from the compact outer layer 32 of bone by a decortication process. The decortication process is performed by abrading the hard outer surface 48 on the compact outer layer 32 of bone to expose an imperforate inner area 50 at a location where the retainer member 20 is to be utilized to form the opening 40 (FIGS. 2 and 3) in the bone 24.

Once the decortication process has been completed, the retainer member 20 is moved through the end portion 28 of the tissue 22 in the manner illustrated schematically in FIG. 1. The retainer member 20 is then pulled toward the right (as viewed in FIG. 1) to obtain a desired level of tension in the tissue 22. This moves the end portion 28 of the tissue 22 from the initial position of FIG. 1 to the connecting position of FIG. 2.

A pointed leading end portion 44 of the retainer member 20 is then moved into engagement with the imperforate inner area 50 on the compact outer layer 32 of bone 24. The retainer member 20 initiates formation of the opening 40. The retainer member 20 is then moved axially through the compact outer layer 32 to the cancellous bone 34 (FIGS. 2 and 3). To move the retainer member 20 through the compact outer layer 32, the retainer member 20 may be rotated about its longitudinal central axis 54 and moved axially into the bone 24 in much the same manner in which a drill is rotated about its central axis and moved into a member being drilled.

It is believed that it will be preferred to move the retainer member 20 into the bone 24 under the influence of an axial force without rotating the retainer member about its central axis 54. Since bone has a relatively high compressive strength, the retainer member 20 formed of bone can be utilized to transmit relatively large forces along the longitudinal central axis 54 of the retainer member 20 to force the retainer member into the bone 24. However, bone has a relatively low tensile strength and cannot transmit large transverse loads. Therefore, when the retainer member 20 is moved into the bone 24 under the influence of axial forces, there may be a tendency for the retainer member to shear or fail by a lateral buckling or fracture of the retainer member rather than by direct compression of the retainer member.

In order to support the retainer member 20 during movement of the retainer member into the bone 24, the retainer member is advantageously inserted into a tubular cylindrical metal sleeve or member 58 (FIG. 2). An annular end portion 62 of the cylindrical sleeve 58 is positioned in engagement with the inner area 50 on the compact outer layer 32 at a location where the retainer member 20 is to be moved into the bone 24. A point on the conical leading end portion 44 of the retainer member engages the inner area 50 on the bone 24 at a location where the formation of the opening 40 is to be initiated.

When the retainer member 20 is to be moved through the tissue 32 into the bone 24, the manner illustrated in FIGS. 1 and 2, the tubular cylindrical sleeve or member 58 is also moved through the end portion 28 of the tissue 22 (FIG. 2). However, if desired, the retainer member 20 could be moved into the bone 24 to the position illustrated in FIG. 3 and the end portion 28 of the tissue then positioned in engagement with the retainer member 20. However, it is believed that it will be preferred to insert the retainer member 20 through the end portion 28 of the tissue 22 before the retainer member is moved into the bone 24 (FIG. 1) so that the retainer member 20 can be utilized to tension the tissue 22.

The tubular member 58 may be moved through the end portion 28 of the tissue 22 (FIG. 2) contemporaneously with the retainer member 20. The conical leading end portion 44 of the retainer member 20 would project from the end of the tubular member 58. This would enable the leading end portion 44 of the retainer member 20 to be utilized to pierce the tissue 22 to initiate the formation of an opening in the tissue. The tubular sleeve 58 can then be utilized to further form the opening in the tissue 22 as the sleeve is moved into the end portion 28 of the tissue. The sleeve 58 may be utilized to apply force to the end portion 28 of the tissue 22 during tensioning of the tissue, that is, during movement of the tissue toward the right (as viewed in FIG. 1).

The retainer member 20 is moved out of the tubular sleeve 58 into the compact outer layer 32 of the bone 24 (FIG. 2). To move the retainer member 20 out of the sleeve 58 into the bone 24, a pusher member 66 is utilized to apply an axial force to a trailing end portion 68 (FIG. 2) of the retainer member 20. The axial force applied by the pusher member 36 has been indicated schematically by an arrow 70 in FIG. 2.

The force 70 applied by the pusher member 66 against the trailing end portion 68 of the retainer member 20 moves the painted leading end portion 44 of the retainer member 20 into the compact outer layer 32 of the bone 24 and initiates the formation of the opening 40. The tubular sleeve 58 engages the cylindrical outer side surface 36 of the retainer member 20 to support the retainer member against sidewise loading. This results in the retainer member being subjected only to compressive forces as the retainer member is forced into the bone 24.

As the retainer member 20 moves into the bone 24, the material of the compact outer layer 32 of a bone is displaced sideways by the leading end portion 44 of the retainer member. As the retainer member 20 continues to move into the compact outer layer 32 of the bone 24, the material of the compact outer layer supports the retainer member 20 against transverse loading in much the same manner as in which the tubular sleeve 58 supports the retainer member 20. Therefore, the pusher member 68 can apply a relatively large axial force to the retainer member 20 without failure, that is without fracture or buckling, of the retainer member 20. The pusher member 66 has a cylindrical outer side surface with the same diameter as the cylindrical outer side surface 36 of the retainer member 20 and of the passage extending through the tubular sleeve 58.

In accordance with another of the features of the present invention, the retainer member 20 is moved through a predetermined distance into the bone 24. During movement of the retainer member 20 into the bone 24 under the influence of the axial force 70, the extent of movement of the retainer member into the bone 24 is determined. The step of moving the retainer member 20 axially into the bone 24 is interrupted when the leading end portion 44 of the retainer member 20 has moved through the compact outer layer 32 of the bone 24 and has moved a predetermined distance into the cancellous bone 34.

In order to enable the extent of penetration of the retainer member 20 into the bone 24 to be determined during movement of the retainer member into the bone, indicia 74 is provided on the pusher member 66. The indicia 74 cooperates with the tubular sleeve 58 to indicate the extent of movement of the retainer member 20 into the bone 24. When the indicia 74 indicates that the retainer member 20 is moved through a desired distance into the bone 24, the application of the force 70 against the retainer member 20 by the pusher member 66 is interrupted.

In the embodiment of the invention illustrated in FIG. 2, the indicia 74 is provided by a plurality of bands of different color on the pusher member 66. Each of the annular bands on the cylindrical pusher member 66 corresponds to a different extent of movement of the retainer member 20 into the bone 24. When a band of a color corresponding to a desired extent of movement of the retainer member 20 into the bone 24 is aligned with an annular upper end 76 of the tubular sleeve 58, the application of the force 70 to the pusher member is interrupted.

It should be understood that although the indicia 74 has been illustrated in FIG. 2 as being formed by annular bands of different colors, the indicia 74 could be formed by suitable alphanumeric characters if desired. Rather than providing the indicia 74 on the pusher member 66, a stop element could be provided on the pusher member. The stop element would be moved into engagement with a selected one of a plurality of slots which have different lengths and extend axially along the tubular sleeve 58. Of course, other methods of indicating the extent of movement of the retainer member 20 into the bone 24 could be utilized if desired.

Once the retainer member 20 has been moved to the desired position relative to the bone 24, the pusher member 66 is removed from the tubular sleeve 58. The tubular sleeve 58 is removed from the end portion 28 of the tissue 22. This results in the tissue 22 being secured against movement relative to the bone 24 by the retainer member 20 (FIG. 3). Therefore, forces resulting from tension in the tissue 22 are transmitted through the retainer member 20 to the bone 24.

The retainer member 20 is effective to secure the tissue 22 against movement relative to the bone 24 during healing of the tissue. Since the retainer member 20 is formed of bone, the retainer member promotes healing and does not have to be removed after the tissue 22 has healed.

The foregoing description has assumed that the retainer member 20 is inserted through the end portion 28 of the tissue 22 and then moved into the bone 24. However, if desired, the retainer member 20 could be moved into the bone 24 prior to engaging the tissue 22. If this was done, the end portion 28 of the tissue 22 would be pulled to tension the tissue and would then be forced downward, as viewed in FIGS. 2 and 3, onto the exposed trailing end portion 68 of the retainer member 20. If desired, a point could be provided on the trailing end portion 68 of the retainer member 20 to facilitate movement of the retainer member into the end portion 28 of the tissue 22.

Figure 4:
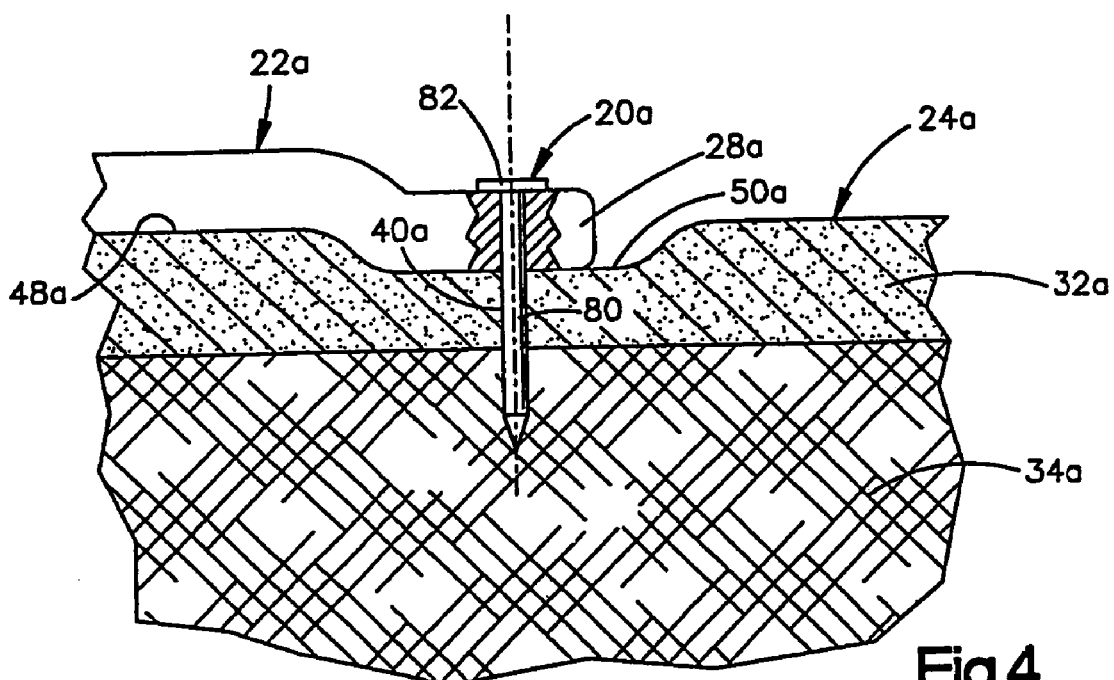
FIG. 4 is a schematic illustration, similar to FIG. 3. Illustrating the manner in which a second embodiment of the retainer member formed of bone is used to secure tissue against movement relative to a bone in a patient's body.

Embodiment of FIG. 4

In the embodiment of the invention illustrated in FIGS. 1-3, a cylindrical retainer member 20 is utilized to secure the tissue 22 against movement relative to the bone 24. In the embodiment of the invention illustrated in FIG. 4, a head end portion is provided on the retainer member to clamp the tissue against the bone. Since the embodiment of the invention illustrated in FIG. 4 is generally similar to the embodiment of the invention illustrated in FIGS. 1-3, similar numerals will be utilized to designate similar components, the suffix letter "a" being added to the numerals of FIG. 4 to avoid confusion.

A retainer member 20a (FIG. 4) is formed of bone and is utilized to secure tissue 22a against movement relative to bone 24a in a human patient's body. The retainer member 20a is also utilized to maintain tension in the tissue 22a. The retainer member 20a has a cylindrical shank portion 80 which extends through an end portion 28a of the tissue 22a. The shank portion 80 of the retainer member 20a extends through a compact outer layer 32a of the bone 24a into cancellous bone 34a which is enclosed by the compact outer layer 32a. The shank portion 80 is utilized to form an opening 40a in the bone 24a.

In accordance with a feature of this embodiment of the invention, the retainer 20a has a circular head end portion 82 which projects radially outward from the cylindrical shank portion 80 and is effective to apply force against the end portion 28a of the tissue 22a. Both the head end portion 82 and the shank portion 80 of the retainer member 20a are formed of bone. The head end portion 82 and the shank portion 80 are formed by a single piece of hard cortical bone which has been freeze dried.

The head end portion 82 of the retainer 20a is effective to clamp the end portion 28a of the tissue 22a against an inner area 50a on the compact outer layer 32a of the bone 24a. The inner area 50a is formed by a decortication process during which a portion of a hard outer surface 48a is removed. Removal of the hard outer surface 48a facilitates penetration of the bone 24a by the retainer member 20a.

The end portion 28a of the tissue 22a is engaged by the shank portion 80 of the retainer member 20a. In the same manner as is illustrated in FIG. 1 for the retainer member 20. The tissue 22a is then tensioned by moving the retainer member 20a and the end portion 28a of the tissue toward the right (as viewed in FIG. 4), in the same manner as is schematically illustrated in FIGS. 1 and 2 for the tissue 22. The shank portion 80 of the retainer member 20a is then utilized to form an opening in the bone 24a.

The head end portion 82 of the retainer member 20a is pressed firmly against the end portion 28a of the tissue 22a to hold the tissue in place and maintain a desired tension in the tissue. Although it is preferred to tension the tissue 22 and 22a of FIGS. 1-4 and to maintain the tension in the tissue with the retainer members 20 and 20a, the retainer members could be utilized to hold the tissue in place without tensioning the tissue.

In the embodiment of the invention illustrated in FIG. 4, the shank portion 80 of the retainer member 20a is utilized to initiate formation of the opening 40a at a location which is free of naturally occurring openings. However, a small pilot opening could be provided in the manner previously described in connection with the embodiment of the invention illustrated in FIGS. 1-3. As was previously mentioned, the pilot opening could be formed with a drill or a long thin member, such as a K-wire. If a long thin member is used to form the pilot opening, the retainer member 20a could be provided with an axial passage extending through the shank portion 80 and the head end portion 82. The long thin member would be inserted through the passage in the retainer member 20a and utilized to guide movement of the retainer member into the bone 24a.

Figure 5:
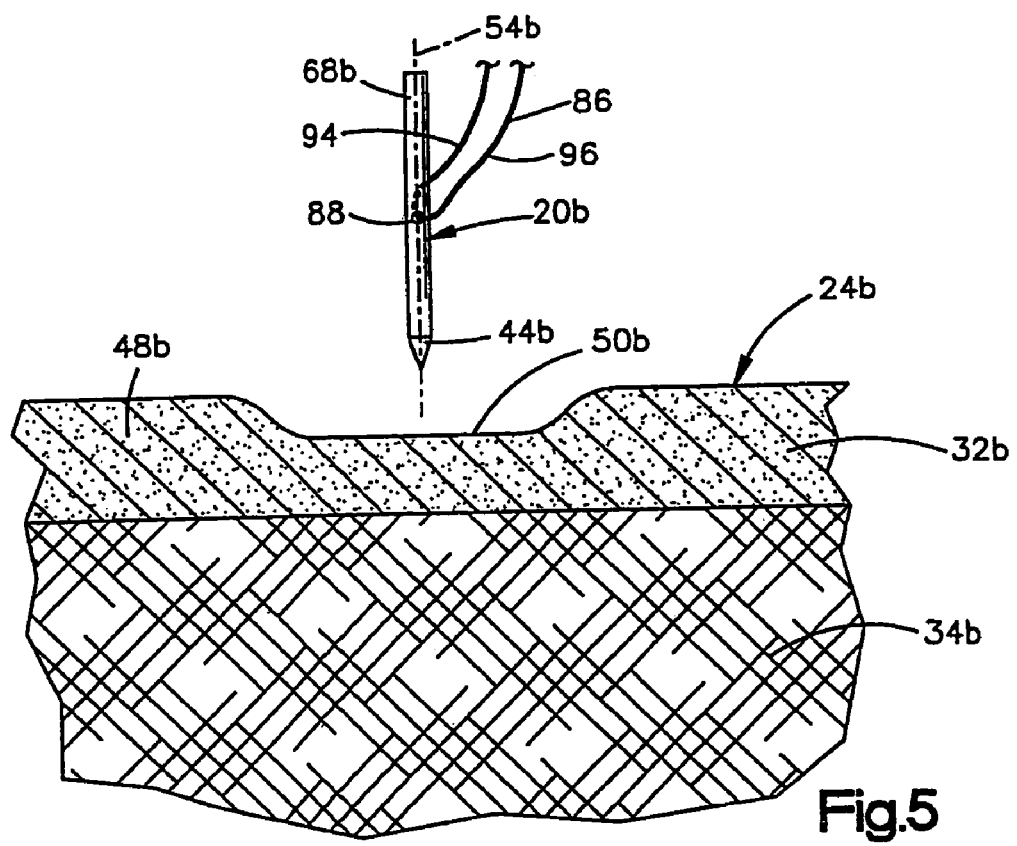
FIG. 5 is a fragmentary schematic illustration, similar to FIG. 1, illustrating the manner in which a retainer member formed of bone is connected with a suture prior to being positioned in a bone in a patient's body.
Figure 6:
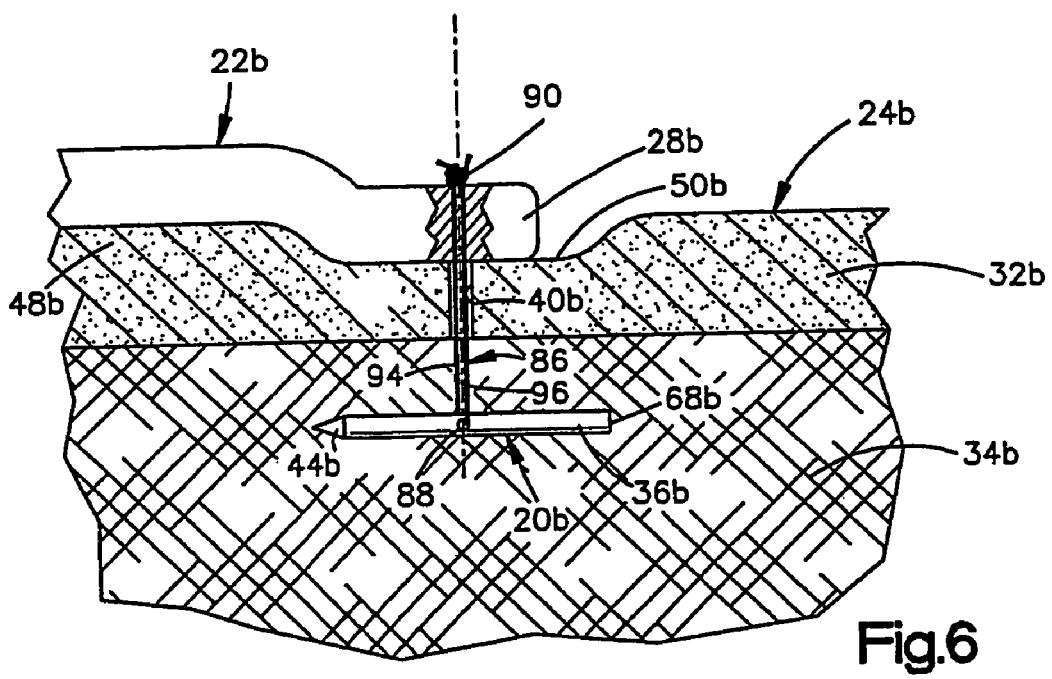
FIG. 6 is a fragmentary schematic illustration, similar to FIG. 5, illustrating the manner in which the retainer member is positioned in the bone in the patient's body and the suture is used to connect tissue with the bone.

Embodiment of FIGS. 5 and 6

In the embodiment of the invention illustrated in FIGS. 1-4, the retainer member 20 formed of bone extends through the tissue 22 to interconnect the retainer member and the bone 24. In the embodiment of the invention illustrated in FIGS. 5 and 6, a retainer member formed of bone is connected with tissue by a suture. Since the embodiment of the invention illustrated in FIGS. 5 and 6 is generally similar to the embodiments of the invention illustrated in FIGS. 1-4, similar numerals will be utilized to designate similar components, the suffix letter "b" being associated with the numerals of FIGS. 5 and 6 to avoid confusion.

A retainer member 20b (FIGS. 5 and 6) is formed of bone. The retainer member 20b may be formed of hard cortical bone which has been freeze dried. The retainer member 20b is utilized to secure tissue 22b (FIG. 6) against movement relative to a bone 24b in a human patient's body.

In accordance with a feature of this embodiment of the invention, a suture 86 is utilized to connect the retainer member 20b with the body tissue 22b. The suture 86 extends through an opening 88 formed in the retainer member 20b. The suture 86 may be connected with the body tissue 22b by a suitable knot 90 (FIG. 6). Alternatively, a fastener or crimp may be utilized to connect end portions of the suture 86. The crimp could have a construction similar to that disclosed in U.S. Pat. No. 5,593,425 which is incorporated by reference.

The retainer member 20b is disposed in cancellous bone 34b. The retainer member 20b is supported by the cancellous bone 34b in a spaced apart relationship with a compact outer layer 32b (FIG. 6) of bone which encloses the cancellous bone 34b. Therefore, the cancellous bone 34b is effective to support the retainer member 20b against movement under the influence of force transmitted to the retainer 20b through the suture 86.

The suture 86 extends through an opening 40b formed in the compact outer layer 32b of the bone 24b. The opening 40b was formed in the bone 24b by the retainer member 20b. The suture 86 extends from the opening 40b into engagement with an end portion 28b of the tissue 22b.

The suture 86 may extend through the end portion 28b of the tissue 22b. In much the same manner as in which the retainer 20 of FIG. 3 extends through the end portion 28 of the tissue 22. Alternatively, sections 94 and 96 of the suture 86 could be wrapped around the tissue 22b to secure the tissue against movement relative to the bone 24b. Tension transmitted through the sections 94 and 96 of the suture 86 is applied to the tissue 22b and firmly clamps or presses the tissue against an inner area 50b formed on the compact outer layer 32b by removing a hard outer surface 48b of the bone 24b with a decortication process.

Tension forces transmitted through the sections 94 and 96 of the suture 86 to the retainer member 20b are transmitted from a cylindrical outer side surface 36b of the retainer member 20b to the cancellous bone 34b. The retainer member 20b is completely enclosed by a matrix of the cancellous bone 34b. Therefore, the outer side surface 36b on the retainer member 20b is pressed against only the cancellous bone 34b under the influence of forces transmitted through the suture 86 to the retainer member 20b. The cancellous bone 34b resists these tension forces and supports the retainer member 20b in a spaced apart relationship with the compact outer layer 32b. This results in the retainer member 20b being supported by the cancellous bone 34b.

The retainer 20b is moved into the bone 24b in the same manner as previously explained in conjunction with the embodiment of the invention illustrated in FIGS. 1-3. However, the retainer 22b is moved completely through the compact outer layer 32b of the bone 24b into the cancellous bone 34b. Once this has occurred, the orientation of the retainer member 20b relative to the bone 24b is changed by rotating the anchor 20b through ninety degrees (90°) with a toggling action in a manner similar to that disclosed in U.S. Pat. Nos. 5,527,343 and 5,534,012.

To position the retainer member 20b relative to the bone 24b, the conical leading end portion 44b (FIG. 5) on the retainer member 20b is moved into engagement with the imperforate inner area 50b on the compact outer layer 32b of the bone 24b. At this time, a central axis 54b of the retainer member 20b extends perpendicular to the surface 50b. An axially directed force, corresponding to the force 70 in FIG. 2, is then applied to the retainer member 20b. This force results in the pointed leading end portion 44b of the retainer member 20b penetrating the compact outer layer 32b of the bone 24b to initiate formation of the opening 40b (FIG. 6).

Continued application of the axial force to the retainer member 20b results in the opening 40b being formed in the compact outer layer 32b of the bone 24b. If desired, a pilot opening could be formed in the compact outer layer 32b of the bone 24b to facilitate locating of the retainer member 20b relative to the bone 24b. The retainer member 20b would then be utilized to enlarge the pilot opening and form the opening 40b as the retainer member 20b is moved axially through the compact outer layer 32b of the bone 24b.

The retainer member 20b is moved completely through the compact outer layer 32b of the bone 24b with the retainer member in the orientation illustrated in FIG. 5, that is, with the central axis 54b of the retainer member extending perpendicular to the inner area 50b on the compact outer layer 32b. Once the retainer member 20b has been moved completely through the compact outer layer 32b, the sections 94 and 96 of the suture 86 are tensioned and the anchor is rotated through 90 to the orientation illustrated in FIG. 6 with a toggling action.

During movement of the retainer member 20b through the compact outer layer 32b of the bone 24b and during formation of the opening 40b, it is contemplated that it may be desirable to support the retainer member 20b with a tubular sleeve, similar to the tubular sleeve 58 of FIG. 2. If this is done, the suture 86 would extend axially through the tubular sleeve. The pusher member 66 of FIG. 2 could be provided with a central opening through which the suture 86 extends or the suture 86 could extend along an outer side of the pusher member. It is contemplated that the pusher member 66 may be moved axially through the outer layer 32b (FIGS. 5 and 6) of the bone 24b to apply force against a trailing end portion 68b of the retainer member 20b during toggling or rotation of the retainer member 20b to the orientation illustrated in FIG. 6. The retainer member 20b may be moved from the orientation shown in FIG. 5 to the orientation shown in FIG. 6 with a toggling action similar to that disclosed in U.S. Pat. Nos. 5,522,846 and 5,534,012, which are both incorporated by reference.

In the embodiment of the invention illustrated in FIGS. 5 and 6, the retainer member 20b is moved through the compact outer layer 32b into the cancellous bone 34b. The orientation of the retainer member 20b is then changed with a togging action. However, it is contemplated that the retainer 20b could be positioned in the bone 24b in a different manner if desired. For example, the retainer 20b could be positioned in the bone 24b in the same manner as previously described in conjunction with the embodiment of the invention illustrated in FIGS. 1-3. If this was done, the trailing end portion 68b of the retainer member 20b would extend from the bone 24b with the axis 54b extending perpendicular to the inner area 50b.

If the retainer 20b is positioned in the manner illustrated in FIGS. 1-3, the suture 86 could extend from a suture opening 88 in the trailing end portion 68b of the retainer member 20b. This would facilitate moving the suture 86 relative to the retainer member 20b when the retainer member is positioned in the bone 24b. The trailing end portion 68b of the retainer 20b would extend outward from the inner area 50b on the compact outer layer 32b of the bone 24b. This would result in the suture opening 88 in the retainer member 20b being exposed so that the bone 24b would not impede movement of the suture 86 relative to the retainer member 20b.

Figure 7:
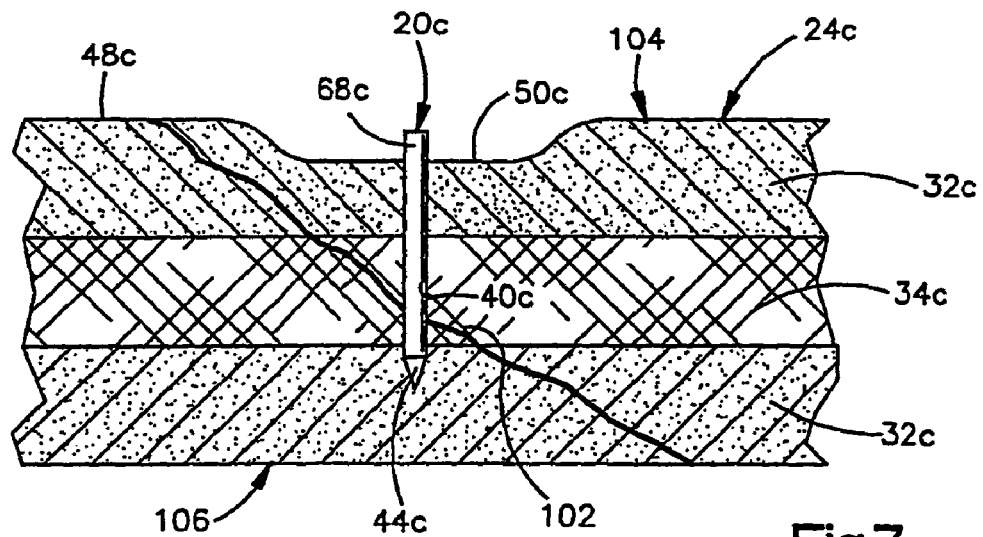
FIG. 7 is a schematic fragmentary sectional view illustrating the manner in which a retainer member formed of bone is used to hold a portion of a bone on one side of a fracture against movement relative to a portion of the bone on the opposite side of the fracture.

Embodiment of FIG. 7

In an embodiment of the invention illustrated in FIGS. 1-6, a retainer member of bone is utilized to position tissue, such as a tendon or ligament, relative to a bone. In the embodiment of the invention illustrated in FIG. 7, a retainer member formed of bone is utilized in the treatment of a fractured bone. Since the embodiment of the invention illustrated in FIG. 7 is generally similar to the embodiment of the invention illustrated in FIGS. 1-6, similar numerals will be utilized to designate similar components, the suffix letter "c" being associated with the numerals of FIG. 7 to avoid confusion.

A bone 24c has a fracture 102 which divides the bone 24c into a first portion 104 at a second portion 106. The two portions 104 and 106 of the bone 24c are formed by a compact outer layer 32c which encloses cancellous bone 34c. A retainer member 20c secures the first and second portions 104 and 106 of the bone 24c against movement relative to each other. The retainer member 20c is formed of bone. The retainer member 20c may be formed of hard cortical bone which has been freeze dried.

The retainer member 20c is positioned in the first portion 104 of the bone 24c. The retainer member 20c extends into the second portion 106 of the bone 24c to connect the second portion 106 of the bone 24c with the first portion 104 of the bone 24c. Thus, the second portion 106 of the bone 24c is tissue which is connected with the first portion 104 of the bone 24c by the retainer member 20c.

The retainer member 20c has the same construction as the retainer member 20 of FIGS. 1-3. The retainer member 20c is positioned in the bone 24c in the same manner as previously explained in conjunction with the embodiment of the invention illustrated in FIGS. 1-3. Thus, the retainer member 20c is utilized to form an opening 40c in the bone 24c. A tubular sleeve, similar to the tubular sleeve 58 of FIG. 2, may be utilized to enclose the retainer member 20c during forming of the opening 40c.

During positioning of the retainer member 20c in the first and second portions 104 and 106 of the bone 24c, the retainer member 20c is utilized to form an opening 40c which extends through the first portion 104 of the bone 24c into the second portion 106 of the bone 24c. In the embodiment of the invention illustrated in FIG. 7, the opening 40c is terminated in the compact outer layer 32c of the second portion 106 of the bone 24c. However, if desired, the opening 40c could extend through both the first portion 104 and the second portion 106 of the bone 24c. If this was done, the retainer member 20c would be moved downward (as viewed in FIG. 7) so that the leading end portion 44c of the retainer member would extend beyond the lower surface of the compact outer layer 32c on the portion 106 of the bone 24c. The leading end portion 44c of the retainer member could then be cut or abraded so that the lower (as viewed in FIG. 7) end of the retainer member 20c would be smooth or flush with the lower (as viewed in FIG. 7) surface of the bone 24c.

When the retainer member 20c is to be positioned relative to the bone 24c, a hard outer surface 48c on the bone 24c is removed with a decortication process. This exposes an imperforate inner area 50c on the compact outer layer 32c of the bone 24c. The retainer member 20c is positioned in a tubular sleeve or member having the same construction as the tubular sleeve or member 58 of FIG. 2. An end portion of the tubular member is positioned adjacent to the inner area 50c with the pointed leading end portion 44c of the retainer member 20c disposed in engagement with the compact outer layer 32c of the bone 24c.

The retainer member 40c is then utilized to form the opening 20c. If desired, a small pilot opening could be formed through the first portion 104 and into the second portion 106 of the bone 24c. The retainer member 20c would then be utilized to form the opening 40c by enlarging the small pilot opening.

To form the opening 40c with the retainer member 20c, a pusher member, corresponding to the pusher member 66 of FIG. 2, is inserted into the tubular sleeve or member, corresponding to the tubular sleeve or member 58 of FIG. 2, in which the retainer member 20c is disposed. Force is then applied against the trailing end portion 68c of the retainer member 20c while the retainer member is supported against sidewise fracturing or buckling by the tubular sleeve.

The leading end portion 44c of the retainer member 20c moves through the compact outer layer 32c on the portion 104 of the bone 24c under the influence of the force applied against the trailing end portion 68c of the retainer member 20c. During the continued application of force to the trailing end portion 68c of the retainer member 20c, the leading end portion 44c of the retainer member moves through the cancellous bone 34c and moves across the fracture 102 into the second portion 206 of the bone 24c. When the leading end portion 44c of the retainer member 20c has moved part way through the compact outer layer 32c on the second portion 106 of the bone 24c to the position illustrated in FIG. 7, the application of force to the trailing end portion 68c of the retainer member 20c is interrupted.

To enable movement of the retainer member 20c into the bone 24c to be interrupted when the retainer member is in the position illustrated in FIG. 7, the extent of movement of the leading end portion 44c of the retainer member 20c relative to the bone 24c is determined during movement of the retainer member 20c into the bone toward the position illustrated in FIG. 7. Determining the extent of movement of the retainer member 20c into the bone 24c may be accomplished by having indicia on the pusher member cooperate with the tubular sleeve which encloses the retainer member 20c during the application of force to the trailing end portion 68c of the retainer member 20c. The manner in which the indicia on the pusher member cooperates with the tubular sleeve to indicate the extent of movement of the leading end portion 44c of the retainer member 20c is the same as was previously discussed in conjunction with the embodiment of the invention illustrated in FIG. 2.

As was previously mentioned, a different method of indicating the extent of movement of the pusher member relative to the tubular sleeve could be utilized, for example, suitable slots in the tubular sleeve could be engaged by a indicator pin extending from the pusher member. Indicia could be provided on the tubular sleeve adjacent to the slots or the slots could have stop surfaces which limit the extent of movement of the pusher member and, therefore, the extent of movement of the retainer member 20c into the bone 24c.

Figure 8:
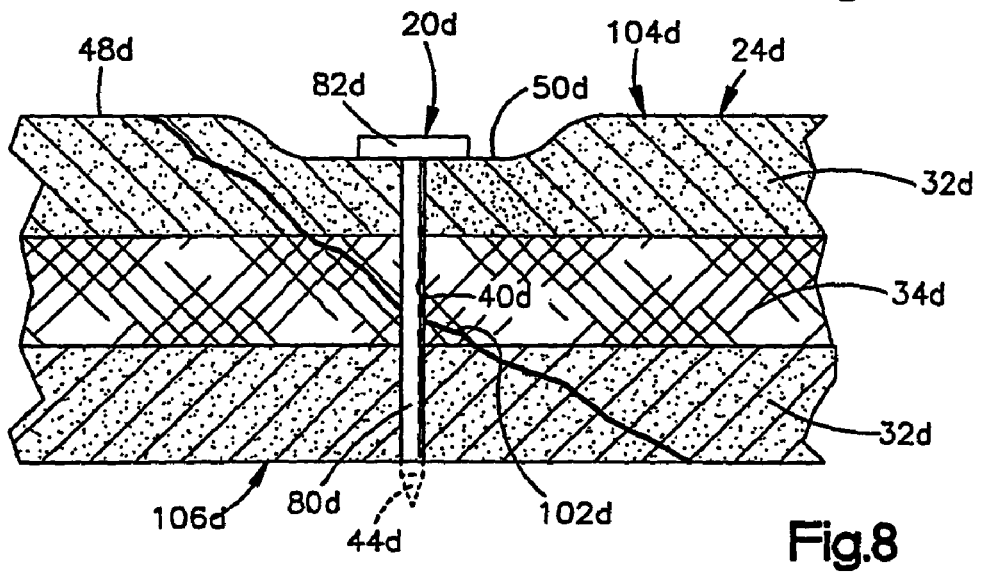
FIG. 8 is a schematic fragmentary sectional view, joined similar to FIG. 7, illustrating the manner in which a second embodiment of the retainer member formed of bone is used to hold a portion of a bone on one side of a fracture against movement relative to a portion of the bone on the opposite side of the fracture.

Embodiment of FIG. 8

The embodiment of the invention illustrated in FIG. 7, a cylindrical retainer member 20c is utilized to treat a fracture 102 in a bone 24c. In the embodiment of the invention illustrated in FIG. 8, the retainer member used to treat the fracture in a bone has a relatively large head end portion. Since the embodiment of the invention illustrated in FIG. 8 is generally similar to the embodiments of the invention illustrated in FIGS. 1-7, similar numerals will utilized to designate similar components, the suffix letter "d" being associated with the numerals of FIG. 8 to avoid confusion.

A retainer member 20d (FIG. 8) is utilized to treat a fracture 102d in a bone 24d. The retainer member 20d has a cylindrical shank portion 80d which extends across the fracture 102d. A circular head end portion 82d is connected with the shank portion 80d. The retainer member 20d is integrally formed as one piece of bone. The retainer member 20d may be formed of hard cortical bone which has been freeze dried.

The fracture 102d divides the bone 24d into a first portion 104d and a second portion 106d. The bone 24d has a compact outer or cortical layer 32d which enclosed cancellous bone 34d. The compact outer layer 32d forms part of the first portion 104d and the second portion 106d of the bone 24d. Similarly, the cancellous bone 34d forms part of both the first and second portions 104d and 106d of the bone 24d.

The fastener 20d is positioned relative to the bone imperforate 24d with the head end portion 82d in engagement with an inner area 50d which is exposed by removing a portion of a hard outer surface 48d on the compact outer layer 32d. A leading end portion 44d on the shank portion 80d of the retainer member 20d is then positioned in engagement with the inner area 50d of the portion 104d of the bone 24d. An axial force is applied against the head end portion 82d of the fastener 20d to move the leading end portion 44d of the fastener through the portion of the compact outer layer 32d disposed on the first portion 104d of the bone 24d.

As force continues to be applied against the head end portion 82d of the fastener 20d, the leading end portion 44d of the fastener 20d moves into the cancellous bone 34d and across the fracture 102d. Movement of the retainer member 20d into the bone 24d is not interrupted until after the shank portion 80d of the retainer member 24d has moved through the portion of the compact outer layer 32d disposed on the portion 106d of the bone 34d. When the fastener 20d has been moved to the position shown in FIG. 8 with the head end portion 82d firmly pressed against the inner area 50d, the leading end portion 44d of the fastener 20d is removed. This results in the leading end of the shank portion 80d being disposed flush with the outer side surface of the second portion 106d of the bone 24d.

During movement of the retainer member 20d into the bone 24d, the shank portion 80d of the retainer member forms an opening 40d which extends through the first portion 104d of the bone 24d. The opening 40d extends across the fracture 102d and through the second portion 106d of the bone 24d. A small pilot opening extending to the bone 24d may be formed prior to movement of the retainer member 20d into the bone 24d. If this is done, the retainer member 20d applies force to the bone 24d to enlarge the small pilot opening and form the relatively large opening 40d in the bone 24d.

Figure 9:
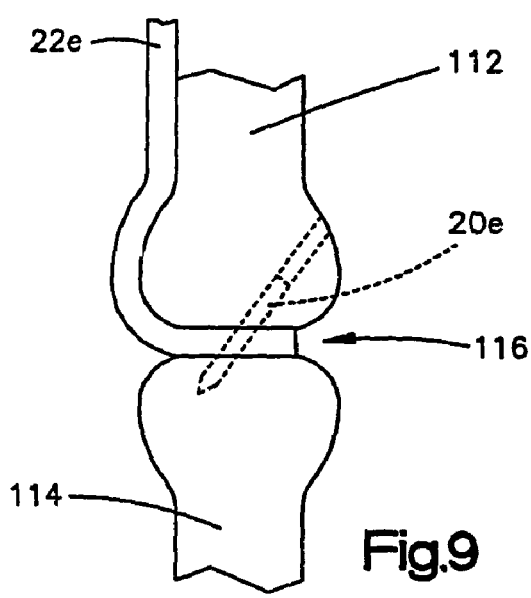
FIG. 9 is a schematic illustration depicting the relationship between end portions of bones in patient's body at a joint between the bones.
Figure 10:
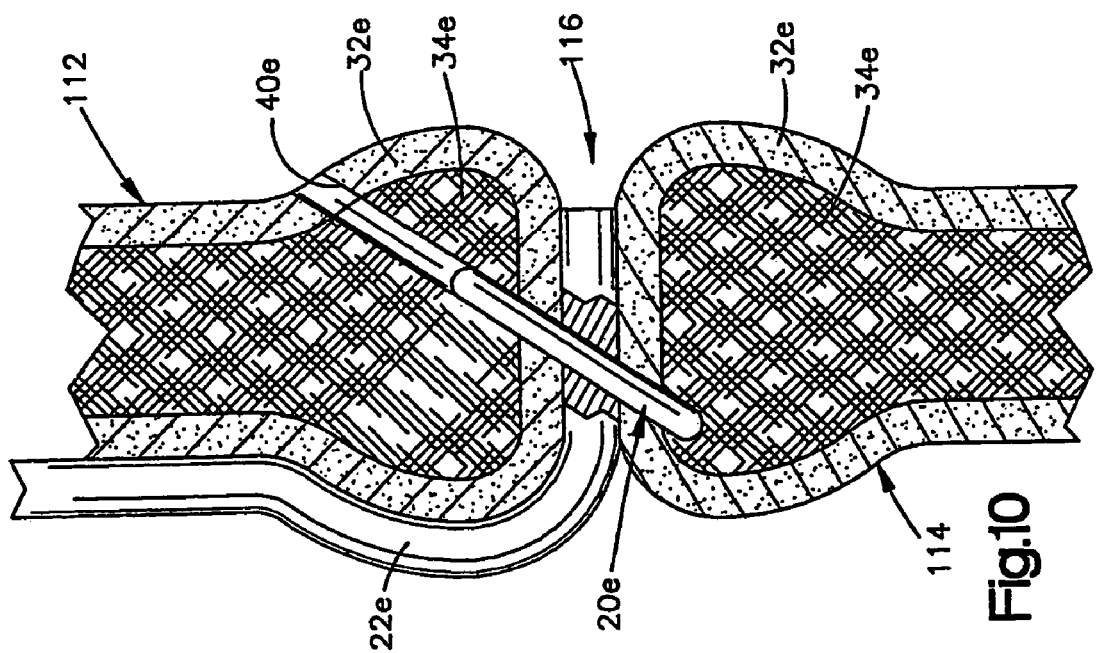
FIG. 10 is an enlarged schematic fragmentary sectional view of the joint of FIG. 9 and illustrating the manner in which a retainer member extends across the joint to immobilize the joint and hold tissue against movement relative to the joint.

Embodiment of FIGS. 9 and 10

In the embodiment of the invention illustrated in FIGS. 1-8, the retainer member has been illustrated as being associated with bone at a location which is spaced at least a short distance from a joint. Of course, the retainer members of FIGS. 1-8 could be associated with bone at a joint if desired. In the embodiment of the invention illustrated. In FIG. 9, a retainer member extends between bones at a joint where the bones are interconnected. Since the embodiment of the invention illustrated in FIGS. 9 and 10 is generally similar to the embodiment of the invention illustrated in FIGS. 1-8, similar numerals will be utilized to designate similar components, the suffix "e" being associated with the numerals of FIGS. 9 and 10 to avoid confusion.

Bones 112 and 114 (FIGS. 9 and 10) are interconnected at a joint 116. Tissue 22e extends along the bone 112 into the joint 116. It is contemplated that the joint 116 may be any one of the many joints in a patient's body.

In accordance with a feature of this embodiment of this invention, a retainer member 20e extends between the bones 112 and 114. The retainer member 20e has a cylindrical configuration. The retainer member 20e is formed from one piece of bone in the same manner as the retainer members 20 of FIGS. 1-8. The retainer member 20e may be formed of hard cortical bone which has been freeze dried. However, the retainer member 20e could be formed of other materials if desired.

The retainer member 20e extends through the tissue 22e to secure the tissue against movement relative to the bones 112 and 114. In addition, the retainer member 20e immobilizes the joint 116. Thus, the retainer member 20e is effective to prevent relative movement between the bones 112 and 114 at the joint 116.

The joint 116 may be permanently immobilized. However, after the tissue 22e has healed. It may be desired to release the bones 112 and 114 for movement relative to each other at the joint 116. This may be accomplished by breaking the retainer member 20e.

To break the bone forming the retainer member 20e, it is merely necessary to move one of the bones, for example the bone 114, relative to the other bone 112. The force transmitted from the bones 112 and 114 to the retainer member 20e will cause the retainer member to break or snap and thereby release the bones 112 and 114 for movement. Since the retainer member 20e is formed of bone, it is not necessary to remove the retainer member from the bones 112 and 114 after the tissue 22e has healed.

The retainer member 20e is positioned in a cylindrical opening 40e which extends through the bone 112 through the tissue 22e and into the bone 114. In the embodiment of the invention illustrated in FIG. 10, the relatively long passage 40e is formed with a drill. However, if desired, the retainer member 20e could be utilized to form the passage 40e in the manner previously described in conjunction with the embodiments of the invention illustrated in FIGS. 1-8.

It is believed, due to the relatively long length of the passage 40e. It may be desired to drill a small diameter pilot passage before using the retainer member 20e to form the passage 40e. A pusher member, corresponding to the pusher member 66 of FIG. 2, would move into the passage 40e to apply force against the retainer member 20e which is illustrated as having a length which is shorter than the passage 40e. If desired, the length of the retainer member 20e could be increased so that a trailing end portion of the retainer member 20e would be flush with the entrance to the passage 40e when the leading end portion of the retainer member is in the position illustrated in FIG. 10. Alternatively, the passage 40e could be drilled only through the bone 112. The remainder of the passage would be formed through the tissue 22e and a portion of the bone 114 by the retainer member 20e.

The bones 112 and 114 have compact outer layers 32e which enclose cancellous bone 34e. The retainer member 20e extends from the cancellous bone 34e in the bone 112 through the compact outer layer 32e of the bone 112 into the tissue 22e. The retainer member 20e extends from the tissue 22e through the compact outer layer 32e of the bone 114. The retainer member 20 extends into the cancellous is bone 34e of the bone 114.

Since the retainer member 20e extends through the tissue 22e, the retainer member is effective to secure the tissue 22e against movement relative to the bones 112 and 114. Since the retainer member 20e extends between the bones 112 and 114, the retainer member is effective to immobilize the joint 116. Of course, immobilization of the joint can be terminated by merely applying sufficient force to the bones 112 and 114 to break the retainer member 20e at the joint 116.

The retainer member 20e is formed of bone. The illustrated embodiment of the retainer 20e is formed of hard cortical bone which has been freeze dried. However, the retainer 20e could be formed of other materials if desired. For example, the retainer 20e could be formed of biodegradable polymers. Alternatively, the retainer 20e could be formed of a ceramic material.

Figure 11:
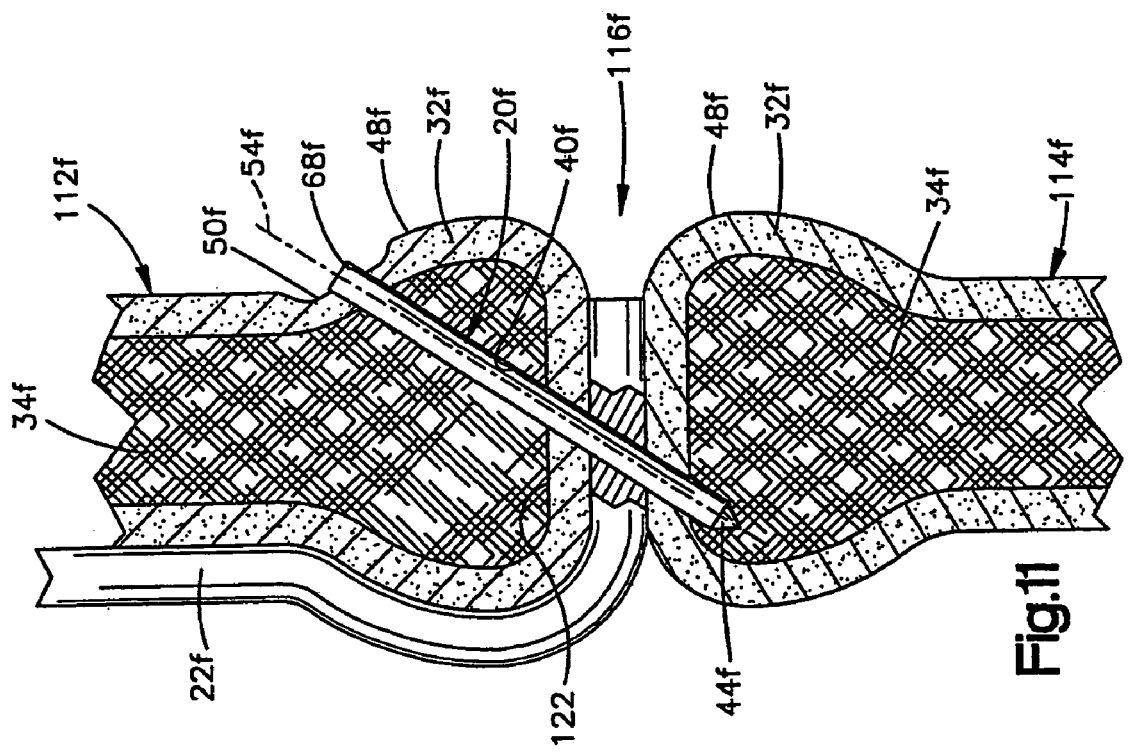
FIG. 11 is a schematic fragmentary sectional view, similar to FIG. 10, illustrating the a manner in which a second embodiment of the retainer member is utilized to immobilize a joint and hold tissue against movement relative to the joint.

Embodiment of FIGS. 11 and 12

In the embodiment of the invention illustrated in FIGS. 9 and 10, a relatively short retainer member 20e extends between bones 112 and 114 to immobilize a joint 116 and to secure tissue 22e against movement relative to the joint. In the embodiment of the invention illustrated in FIGS. 11 and 12, a relatively long retainer member is provided to immobilize the joint and hold tissue against movement relative to the joint. Since the embodiment of the invention illustrated in FIGS. 11 and 12 is generally similar to the embodiment of the invention illustrated in FIGS. 1-10, similar numerals will be utilized to designate similar components, the suffix letter "f" being associated with the numerals of FIGS. 11 and 12.

Bones 112f and 114f are interconnected at a joint 116f. Tissue 22f extends into the joint 116f and is disposed between the ends of the bones 112f and 114f. A retainer member 20f extends between the bones 112f and 114f and extends through the tissue 22f at the joint 116f. The retainer member 20f immobilizes the joint, that is, the retainer member secures the bones 112f and 114f against movement relative to each other. In addition, the retainer 20f secures the tissue 22f against movement relative to the bones 112f and 114f at the joint 116f.

In accordance with one of the features of the present invention, the retainer member 20f is formed of bone. The retainer member 20f may be formed of hard cortical bone which has been freeze dried. The retainer member 20f is utilized to form an opening 40f which extends through the bone 112f, through the tissue 22f, and into the bone 114f. If desired, the retainer member 20f could extend through the bone 114f and have a lower (as viewed in FIG. 11) end which is flush with an outer side surface of the bone.

The retainer member 20f has a cylindrical configuration and is integrally formed as one piece of bone. The retainer member 20f has a pointed leading end portion 44f which initiates formation of the opening 40f. If desired, a relatively small diameter pilot opening could be drilled through the bone 112f, body tissue 22f into the bone 114f. The retainer member 20f would then be utilized to form the opening 40f by enlarging the small pilot opening. In the embodiment of the invention illustrated in FIG. 10, it is contemplated that it may be preferred to form the opening 40e with a drill. However, In the embodiment of the invention illustrated in FIGS. 11 and 12. It is contemplated that it will be preferred to utilize the retainer member 20f to form the opening 40f.

When the retainer member 20f is to be positioned in the bones 112f and 114f, a hard outer surface 48f of a compact outer layer 32f of the bone 112f is ground or abraded away with a decortication process. This exposes an imperforate inner area 50*f* on the compact outer layer 32*f* of the bone 112*f*. The leading end portion 44*f* of the retainer member 20*f* is then positioned in engagement with the inner area 50*f*.

A force, corresponding to the force 70 of FIG. 2, is then applied to a trailing end portion 68*f* of the retainer member 20*f*. The retainer member 20*f* may be enclosed with a tubular member, corresponding to the tubular member 58 of FIG. 2. Force may be applied against the trailing end portion 68*f* of the retainer member 20*f* with a pusher member, corresponding to the pusher member 66 of FIG. 2. The force applied to the trailing end portion 68*f* of the retainer member 20*f* extends parallel to a longitudinal central axis 54*f* of the retainer member 20*f*.

The force applied to the trailing end portion 68*f* of the retainer member 20*f* causes the pointed leading end portion 44*f* of the retainer member to initiate the formation of the opening 40*f* in the compact outer layer 32*f* of the bone 112*f*. The force applied to the trailing end portion 68*f* of the retainer member 20*f* moves the leading end portion 44*f* of the retainer member through the compact outer layer 32*f* into cancellous bone 34*f* which is enclosed by the compact outer layer 32*f*.

The continued application of force to the trailing end portion 68*f* of the retainer member 20*f* moves the retainer member through the cancellous bone 34*f*. The leading end portion 44*f* of the retainer member 20*f* moves into engagement with an inner side surface 122 of the compact outer layer 32*f*. The pointed leading end portion 44*f* then penetrates the compact outer layer 32*f* for a second time. This results in the formation of an opening 40*f* which extends through the bone 112*f*.

The leading end portion 44*f* of the retainer member 20*f* then enters the tissue 22*f*. The continued application of force against the trailing end portion 68*f* of the retainer member 20*f* moves the leading end portion 44*f* into the compact outer layer 32*f* on the bone 114*f*. If desired, a hard outer surface 48*f* on the compact outer layer 32*f* of the bone 114*f* could be removed with a decortication process at the location where the leading end portion 44*f* of the retainer member 20*f* moves into initial engagement with the bone 114*f*.

The continued application of force against the trailing end portion 68*f* of the retainer member 20*f* moves the retainer member through the compact outer layer 32*f* of the bone 114*f* into cancellous bone 34*f*. Movement of the retainer member 20*f* into the bone 114*f* can be terminated with the leading end portion 44*f* in the cancellous bone 34*f* of the bone 114*f*, as shown in FIG. 11. However, if desired, the movement of the retainer member 20*f* along its longitudinal central axis 54*f* could be continued and the retainer member moved through the compact outer layer 32*f* of the bone 114*f* for a second time.

When the retainer member 20*f* is moved through the bone 112*f* and the tissue 22*f* into the bone 114*f*, a shown in FIG. 11, the retainer member immobilizes the joint 116*f*. In addition, the retainer member 20*f* secures the tissue 22*f* in the joint 116*f*.

During movement of the retainer member 20*f* into and through the bone 112*f* into and through the tissue 22*f* and into the bone 114*f*, it is believed that it may be preferred to enclose the portion of the retainer member 20*f* which is disposed outside of the opening 40*f* with a tubular sleeve or member, corresponding to the tubular sleeve or member 58 of FIG. 2. The end of the tubular member would be positioned in engagement with the inner area 50*f* on the compact outer layer 32*f* of the bone 112*f*. A pusher member, corresponding to the pusher member 66 of FIG. 2, would be utilized to apply force against the trailing end portion 68*f* of the retainer member 20*f*.

It is believed that it would be particularly advantageous to utilize indicia which indicates the extent to which the leading end portion 44*f* of the retainer member 20*f* is moved along the central axis 54*f*. This is because the opening 40*f* has a relatively long axial extent and the use of indicia, corresponding to the indicia 74 of FIG. 2, on the pushrod will enable a surgeon to determine exactly where the leading end portion 44*f* of the retainer member 20*f* is located relative to the bones 112*f* and 114*f*. The indicia will also allow the surgeon to terminate movement of the retainer member 20*f* along the axis 54*f* when the retainer member is moved to the position shown in FIG. 11.

After the joint 116*f* has been immobilized for a sufficient period of time to enable the tissue 22*f* to heal. It is contemplated that it may be desired to release the joint 116*f* so that the bones 112*f* and 114*f* can move relative to each other at the joint. To release the joint 116*f*, force is applied to the bones 112*f* and 114*f* to break the retainer member 20*f* in the manner illustrated schematically in FIG. 12. Thus, force applied to the bones 112*f* and 114*f* tends to rotate the bone 114*f* in a counterclockwise direction from the position illustrated in FIG. 11 to the position shown in FIG. 12. As this occurs, the force applied to the retainer member 20*f* causes the retainer member to break or fracture at a location indicated schematically at 126 in FIG. 12. Since the retainer member 20*f* is formed of bone which is relatively weak in tension, a relatively small amount of force is required to break the retainer member 20*f*. Since the retainer member 20*f* is formed of bone, there is no need to remove the retainer member after it has been broken.

Embodiment of FIG. 13

In the embodiment of the invention illustrated in FIGS. 11 and 12, the retainer member 20*f* is utilized to initiate the formation of the opening 40*f* and to form the opening. In the embodiment of the invention illustrated in FIG. 13, a guide wire or rod is utilized to initiate formation of the opening which is subsequently formed by the retainer member. Since the embodiment of the invention illustrated in FIG. 13 is generally similar to the embodiment of the invention illustrated in FIGS. 1-12, similar numerals will be utilized to designate similar components, the suffix letter "g" being associated with the numerals of FIG. 13 to avoid confusion.

Tissue 22*g* (FIG. 13) is disposed between bones 112*g* and 114*g* at a joint 116*g*. A retainer member 20*g* is utilized to secure the tissue 22*g* against movement relative to the bones 112*g* and 114*g* and to secure the bones against movement relative to each other. The retainer member 20*g* has a cylindrical configuration and is formed of bone. The retainer member 20*g* may be formed of hard cortical bone which has been freeze dried.

In accordance with one of the features of the embodiment of the invention illustrated in FIG. 13, a cylindrical guide wire or rod 132 extends through a cylindrical passage 134 formed in the retainer member 20*g*. The guide wire or rod 132 forms small diameter pilot openings which extend through the bone 112*g*, through the tissue 22*g* at the joint 116*g* and into the bone 114*g*. The guide wire or rod 132 is moved to the position illustrated in FIG. 13 to form the relatively small diameter pilot openings while the retainer member 20*g* is spaced apart from the guide wire or rod. To move the guide wire or rod 132 to the position shown in FIG. 13, an axial force is applied against the guide wire.

Once the guide wire 132 has been moved through the bone 112*g*, the tissue 22*g*, and into the bone 114*g* in the manner illustrated in FIG. 13, the retainer member 20*g* is moved into telescopic engagement with the guide wire 132. To provide for engagement of the guide wire 132 with the retainer member 20*g*, the upper (as viewed in FIG. 13) end of the guide wire 132 is inserted into the cylindrical passage 134 which extends axially through the retainer member 20g. The retainer member 20g is then moved, axially along the guide wire 132 until a conical leading end portion 44g of the retainer member 20g engages an inner area 50g on the compact outer layer 32g of the bone 112g. The inner area 50g is formed by abrading or otherwise removing a hard outer surface layer 48g from the compact outer layer 32g with a decortication process.

Once the retainer member 20g has been moved along the guide wire 132g into engagement with the compact outer layer 32g of the bone 112g, a tubular sleeve or member 58g is moved along the guide wire rod 132 into telescopic engagement with the retainer member 20g. An annular leading end portion 62g of the tubular sleeve 58g is moved into engagement with the area 50g in the manner illustrated in FIG. 13. At this time, the leading end portion 44g of the retainer member 20g is also disposed in engagement with the area 50g on the compact outer layer 32g of the bone 12g.

The tubular sleeve 58g has an axial extent which is greater than the axial extent of the retainer member 20g. Therefore, the tubular sleeve 50g extends axially past an upper or trailing end portion of the retainer member 20g. At this time, the retainer member 20g is fully enclosed by the tubular sleeve 58g.

A pusher member 66g has a longitudinally extending cylindrical passage 138 through which the guide wire rod 132 extends. When the leading end portion 44g of the retainer member 20g is disposed in engagement with the inner area 50g, the tubular sleeve 58g encloses the retainer member. The pusher member 66g extends axially upward (as viewed in FIG. 13) from the upper end portion of the tubular sleeve or member 58g.

In order to form the opening 40g with the retainer member 20g, force. Indicated schematically by arrows 70g in FIG. 13, is applied against the upper (as viewed in FIG. 13) end of the pusher member 66g. The force is transmitted from the pusher member 66g to the retainer member 20g. The force transmitted to the retainer member 20g causes the leading end portion 44g of the retainer member 20g to form the opening 40g in the compact outer layer 32g of the bone 112g.

As the opening 40g is formed in the compact outer layer 32g of the bone 112g by the retainer member 20g, the retainer member is moved axially along the guide wire 132. Therefore, the guide wire 132 is effective to steer movement of the retainer member 20g through the bone 112g and tissue 22g into the bone 114g. As the force 70g applied by the pusher member 66g to the trailing end of the retainer member 20g moves the retainer member 20g into cancellous bone 34g of the bone 112g, the guide wire 132 cooperates with the retainer member 20g to prevent deviation of the retainer member from its intended course.

Continued movement of the retainer member 20g along the guide wire 132 under the influence of force 70g, results in the leading end portion 44g of the retainer member 20g moving into engagement with an inner side surface 122g of the compact outer layer 32g on the bone 112g. Continued application of axial force to the retainer member 20g moves the retainer member along the guide wire 132 through the compact outer layer 32g and into the tissue 22g. The leading end portion 44g of the retainer member 20g then moves into engagement with the compact outer layer 32g of the bone 114g.

Continued movement of the retainer member 20g along the guide wire 132 moves the leading end portion 44g of the retainer member through the compact outer layer 32g of the bone 114g. The leading end portion 44g of the retainer member 20g then moves into cancellous bone 34g which is enclosed by the compact outer layer 32g of the bone 114g.

Indicia, corresponding to the indicia 74 of FIG. 2, on the pusher member 66g cooperates with the tubular sleeve 58g to indicate when the leading end portion 44g of the retainer member 20g has reached the lower (as viewed in FIG. 13) end of the guide wire 132. When this happens, an application of the force 70g to the pusher member 66g is interrupted and axial movement of the retainer member 20g along the guide wire 132 is interrupted. At this time, a trailing end portion of the retainer member 20g will have reached the end of the tubular sleeve 58 and be adjacent to the inner area 50g on the compact outer layer 32g of the bone 112g.

The tubular sleeve 58g and pusher member 66g are then disengaged from the guide wire 132 by moving them axially upward (as viewed in FIG. 13) away from the bone 112g along the guide wire. The guide wire 132 is then withdrawn from the retainer member 20g.

After the guide wire 132 is withdrawn from the retainer member 20g, the retainer member is disposed in the same orientation relative to the bones 112g and 114g as is the retainer member 20f relative to the bones 112f and 114f of FIG. 11. Thus, the retainer member 20g will extend through the bone 112g and through the body tissue 22g into the bone 114g. If desired, the retainer member 20g could be moved through the bone 114g so that the leading end portion 44g of the retainer member 20g extends from the outer side surface of the bone 114g. The leading end portion 44g of the retainer member would then be removed so that the end of the retainer member 20g would be aligned with the outer side surface of the bone 114g to provide a smooth area which would not irritate adjoining tissue. If the retainer member 20g is to extend through the bone 114g, the guide wire 132 would be moved through the bone 114g to enable the guide wire to guide movement of the retainer member 20g throughout the extent of axial movement of the retainer member relative to the bone 114.

Once the retainer member 20g has been moved to the desired position relative to the bones 112g and 114g, that is to a position corresponding to the position of the retainer member 20f of FIG. 11 relative to the bones 112f and 114f, the joint 116g is immobilized. Thus, the bones 112g and 114g are secured against movement relative to each other. In addition, the tissue 22g is secured against movement relative to the bones 112g and 114g.

In the embodiment of the invention illustrated in FIG. 13, the retainer member 20g is formed of bone. However, the retainer member 20g may be formed of other materials if desired. For example, the retainer member 20g could be formed of a biodegradable material. Alternatively, the retainer member 20g could be formed of a ceramic material.

CONCLUSION

In view of the foregoing description. It is apparent that the present invention relates to a new and improved method of securing tissue 22 against movement relative to a portion of a bone 24 in a patient's body. The method includes positioning a retainer member 20 formed of bone in the portion of the bone 24 in the patient's body and connecting the retainer member with the tissue 22 to be secured. The step of positioning the retainer member 20 formed of bone in the patient's body may include utilizing the retainer member to form an opening 40 in a compact outer layer of the portion of the bone 24 in the patient's body.

When the retainer member 20 formed of bone is used to form an opening 40 in the portion of the bone 24 in the patient's body, the retainer member may advantageously be at least partially enclosed in a tubular member 58. Force 70 may be applied against a trailing end portion 68 of the retainer member 20 formed of bone to force a leading end portion 44 of retainer member into the portion of the bone 24 in the patient's body. Movement of the retainer member 20 into the portion of the bone 24 in the patient's body may advantageously be interrupted when the leading end portion 44 of the retainer member has moved to a predetermined depth in the bone in the patient's body.

The retainer member 20 formed of bone may extend through and/or tension body tissue 22 which is to be connected with the bone 24 in the patient's body by the retainer member. The retainer member 20 formed of bone may have a head end portion 82 which engages body tissue 22. Alternatively, the retainer member 20 formed of bone may be utilized to anchor a suture 86 which is connected with body tissue. The retainer member 20 formed of bone may be positioned in a bone 24 in the patient's body so as to extend across a fracture 102 and hold the portions 104 and 106 of the bone on opposite sides of the fracture against movement relative to each other.

A retainer member 20, which may or may not be formed of bone, is utilized to immobilize a joint 116 by having the retainer member extend between bones 112 and 114 at the joint. If it is subsequently desired to release the joint 116 for movement, the retainer member may be broken.

What is claimed is:

1. A method of resisting movement of tissue relative to a portion of a bone in a patient's body, said method comprising the steps of: positioning a tubular member through at least a portion of the tissue; wherein the tubular member is at least partially tubular; passing at least a portion of a retainer body through at least a portion of the tubular member through the tissue and into the portion of the bone by applying a force to the retainer; contacting the retainer with the tissue and bone, wherein the retainer body extends from the tissue into the bone to resist movement of the tissue relative to the bone.

2. A method as set forth in claim 1 wherein said step of passing at least a portion of the retainer includes initiating formation of an opening in a cortical portion of the bone in the patient's body.

3. A method as set forth in claim 1 further including the step of removing a hard surface area from a location on the portion of the bone in the patient's body, said step of passing at least a portion of the retainer includes transmitting force from an end portion of the retainer to the portion of the bone in the patient's body at the location where the hard surface area was removed.

4. A method as set forth in claim 1 wherein said step of passing at least a portion of the retainer includes:
applying an axially directed force against the retainer without rotating the retainer about a central axis of the retainer.

5. A method as set forth in claim 1 wherein said step of passing at least a portion of the retainer includes:
moving at least a portion of the retainer body into cancellous bone enclosed by a compact outer layer.

6. A method as set forth in claim 1 wherein said steps of passing at least a portion of the retainer and engaging the retainer include moving a portion of the retainer through the portion of the bone in the patient's body into the tissue to be secured.

7. A method as set forth in claim 1 wherein the bone in the patient's body is divided into a first portion and a second portion by a fracture and the tissue is the second portion of the bone, said steps of passing at least a portion of the retainer and engaging the retainer include moving a portion of the retainer through the first portion of the bone into the second portion of the bone.

8. A method as set forth in claim 1 wherein the portion of a bone in the patient's body is a first bone and the tissue is a second bone in the patient's body, said steps of passing at least a portion of the retainer and engaging the retainer include
moving a portion of the retainer through the first bone into the second bone to prevent relative movement between the first and second bones.

9. A method as set forth in claim 8 further including the step of breaking the retainer to enable relative movement to occur between the first and second bones.

10. A method as set forth in claim 1 wherein said step of engaging includes transmitting force between the tissue and the retainer through a suture.

11. A method as set forth in claim 10 wherein said step of engaging includes moving the retainer through a compact outer layer of bone into cancellous bone and
changing an orientation of the retainer relative to the compact outer layer of bone after performing said step of moving the retainer through the compact outer layer into cancellous bone.

12. A method as set forth in claim 1 wherein said step of engaging the retainer includes:
moving a leading end portion of the retainer into the portion of the bone in the patient's body and
interrupting movement of the retainer into the portion of the bone in the patient's body when the leading end portion of the retainer has moved a predetermined distance into the portion of the bone disposed in the patient's body.

13. A method as set forth in claim 12 wherein said step of passing at least a portion of the retainer includes
engaging a trailing end portion of the retainer with a pusher member, said step of passing at least a portion of the retainer being interrupted when the pusher member is in a predetermined position relative to the tubular member.

14. A method as set forth in claim 13 wherein
one of the pusher member and tubular member is provided with a stop and
the other of the pusher member and tubular member is provided with at least one slot, the stop engaging an end portion of the at least one stop to limit movement of the pusher member with respect to the tubular member.

15. A method as set forth in claim 14 wherein
the pusher member is provided with the stop and
the tubular member is provided with a plurality of slots, each slot having a different length.

16. A method as set forth in claim 12 wherein said step of passing at least a portion of the retainer includes:
forming an opening in the portion of the bone in the patient's body with a leading end portion of the retainer.

17. A method as set forth in claim 1 wherein said step of passing at least a portion of the retainer includes
moving a thin elongated member into the portion of the bone in the patient's body and
guiding movement of the retainer into the portion of the bone in the patient's body with the thin elongated member.

18. A method as set forth in claim 1 further including the step of:
disengaging the tubular member from the tissue and the retainer after performing said step of engaging the retainer with the tissue and the portion of the bone in the patient's body.

19. A method as set forth in claim 18 wherein said step of passing at least a portion of the retainer includes
applying an axially directed force against the retainer and pushing material of the portion of the bone in the patient's body aside under the influence of the axially directed force without rotating the retainer about a central axis of the retainer.

20. The method according to claim 1, which further comprises shaping said retainer with a cylindrical outer surface.

21. The method according to claim 20, wherein said cylindrical outer surface is notchless.

22. The method of claim 1, further including, prior to said step of applying, the steps of:
initiating an opening in bone of the patient using a long thin guide member, a portion of the long thin guide member thereafter extending from the bone;
accepting the long thin guide member through an axially extending passage formed through an elongated retainer member formed of bone.

23. The method of claim 1, wherein in said positioning step, said retainer has a cylindrical cross section, and is positioned within the tubular member.

24. The method of claim 1, including the steps of:
prior to said step of applying a force, the step of predrilling a pilot opening, sized substantially smaller than the retainer, through the bone; and
in said step of applying a force, the step of enlarging the pilot opening with the retainer.

25. The method of claim 1, wherein the retainer includes tissue selected from the group consisting of: freeze dried bone, hard cortical bone, ligamentous tissue, and tendenous tissue.

26. The method of claim 1, further including, prior to said step of applying a force, the step of engaging the portion of the bone with the tubular member.

27. The method of claim 1, further including the step of moving the tubular member through body tissue of the patient.

28. The method of claim 1, wherein passing at least a portion of a retainer includes applying an axially directed force to the retainer, thereby moving at least a portion of the retainer out of the tubular member and into bone, the tubular member engaging the outer side surface of the retainer to support the retainer against transverse forces relative to the longitudinal axis of the retainer, while the retainer is passed.

29. A method of securing tissue against movement relative to a portion of a bone in a patient's body, said method comprising positioning a retainer comprising a retainer body in a supporting sleeve which engages the outer side surface of the retainer to support the retainer against transverse forces relative to the longitudinal axis of the retainer body; moving at least a portion of the retainer out of the supporting sleeve with an axially directed force into an initial opening formed by the retainer body, and into and disengaging the supporting sleeve from the tissue to be secured and the retainer after performing said act of moving at least a portion of the retainer into the portion of the bone in the patient's body; wherein the retainer body contacts the tissue and the bone; and wherein the retainer body extends from the tissue into the bone and secures the tissue to the bone to thereby resist movement of the tissue relative to the bone.

30. The method according to claim 29, which further comprises shaping said retainer with a cylindrical outer surface.

31. The method of claim 29, further including, prior to said step of passing, the steps of:
initiating an opening in bone of the patient using a long thin guide member, a portion of the long thin guide member thereafter extending from the bone;
accepting the long thin guide member through an axially extending passage formed through an elongated retainer.

32. The method of claim 29, wherein the bone in the patient's body is divided into a first portion and a second portion by a fracture and the tissue to be secured is the second portion of the bone, said steps of moving at least a portion of the retainer out of the supporting sleeve into the portion of the bone in the patient's body and connecting the retainer with the tissue to be secured include moving a portion of the retainer through the first portion of the bone into the second portion of the bone.

33. The method of claim 29, wherein the retainer is formed with a material selected from the group consisting of: bone, allograft bone, autograft bone, heterograft bone, freeze dried bone, biodegradable polymer, and ceramic.

34. A method of securing tissue to resist movement relative to a portion of a bone in a patient's body, said method comprising the steps of: positioning a retainer comprising a body formed of bone within a supporting sleeve which slidably engages the outer side surface of the retainer to support the retainer against transverse forces relative to the longitudinal axis of the retainer; and applying an axially directed force to the retainer, thereby sliding at least a portion of the retainer through the supporting sleeve as the portion of the retainer body is moved into the portion of the bone in the patient's body without applying a twisting force, a portion of the retainer body extending from the bone into the tissue to be secured, and contacting the retainer body with the tissue and bone to be secured; wherein an axial compressive force along the longitudinal axis of the retainer may be applied without causing failure of the retainer due to transverse or twisting forces.

35. A method of connecting tissue to resist movement of the tissue relative to a portion of a bone in a patient's body, comprising: positioning a supporting sleeve proximate a portion of the tissue to be connected; applying an axially directed force to a retainer having a body, thereby pushing at least a portion of a retainer body into bone of the patient's body, forming an opening for passage of the retainer body in a cortical surface of the bone, at least a portion of the retainer body supported within the supporting sleeve, the supporting sleeve engaging the outer side surface of the retainer body to support the retainer body against transverse forces relative to the longitudinal axis of the retainer while the retainer is pushed; and wherein an axial compressive force along the longitudinal axis of the retainer may be applied without causing failure of the retainer due to transverse forces; and whereby a portion of the retainer body contacts the tissue and the bone, and a portion of the retainer body is disposed within the bone, thereby connecting the tissue to the bone.

* * * * *